(12) United States Patent
Sun et al.

(10) Patent No.: US 12,129,505 B2
(45) Date of Patent: Oct. 29, 2024

(54) OLEAGINOUS YEAST AND ITS APPLICATION

(71) Applicant: Jiangnan University, Wuxi (CN)

(72) Inventors: Fubao Sun, Wuxi (CN); Qiuli Zhou, Wuxi (CN); Yun Hu, Wuxi (CN); Hongyan Ren, Wuxi (CN); Chihe Sun, Wuxi (CN)

(73) Assignee: Jiangnan University, Wuxi (CN)

( * ) Notice: Subject to any disclaimer, the term of this patent is extended or adjusted under 35 U.S.C. 154(b) by 359 days.

(21) Appl. No.: 17/674,913

(22) Filed: Feb. 18, 2022

(65) Prior Publication Data

US 2022/0170058 A1  Jun. 2, 2022

Related U.S. Application Data

(63) Continuation of application No. PCT/CN2021/094555, filed on May 19, 2021.

(30) Foreign Application Priority Data

Jun. 15, 2020 (CN) .......................... 202010546363.0

(51) Int. Cl.
| | | |
|---|---|---|
| C12P 7/6409 | (2022.01) | |
| C12N 1/16 | (2006.01) | |
| C12N 1/22 | (2006.01) | |

(52) U.S. Cl.
CPC .............. *C12P 7/6409* (2013.01); *C12N 1/16* (2013.01); *C12N 1/22* (2013.01)

(58) Field of Classification Search
CPC ... C12P 7/6409; C12P 2203/00; C12P 7/6463; C12P 2201/00; C12N 1/16; C12N 1/22; C12N 1/165; C12N 1/38; C12N 1/145; C12R 2001/645

See application file for complete search history.

(56) References Cited

FOREIGN PATENT DOCUMENTS

| | | |
|---|---|---|
| CN | 102634549 A | 8/2012 |
| CN | 103642858 A | 3/2014 |
| CN | 111635867 A | 9/2020 |

OTHER PUBLICATIONS

Houmin Li, et. al., "Micorbiological characteristics of medically important *Trichosporon* species" China J Lab Med Jun. 2005, vol. 28, No. 6.

Chao Huang, et. al., "Oil production by the yeast *Trichosporon dermatis* cultured in enzymatic hydrolysates of corncobs" Bioresource Tech 110 (2012) 711-714, Jan. 24, 2012.

*Primary Examiner* — Satyendra K Singh
(74) *Attorney, Agent, or Firm* — IPRO, PLLC; Na Xu

(57) ABSTRACT

Disclosed is oleaginous yeast and its application, belonging to the technical field of microorganisms. The oleaginous yeast provided by the disclosure has been deposited in China Center for Type Culture Collection on May 21, 2020, with an accession number of CCTCC NO: M 2020139. The oleaginous yeast provided by the disclosure can use a hydrolysate of cheap lignocellulose biomass as the substrate. Xylose and glucose in the hydrolysate are simultaneously utilized to produce oil, so the sugar utilization efficiency and production intensity are enhanced. After 8 days of fed-batch fermentation, the oil yield can reach 31.33 g/L, and the oil content can reach 60.83%. The waste resources can be reutilized, and the production cost is reduced, so the oleaginous yeast has wide application prospects.

7 Claims, 2 Drawing Sheets

OLEAGINOUS YEAST AND ITS APPLICATION

TECHNICAL FIELD

The disclosure relates to oleaginous yeast and its application, belonging to the technical field of microorganisms.

BACKGROUND

Some microorganisms, such as yeasts, bacteria, molds and microalgae, can use carbohydrates, hydrocarbons and oil as carbon sources to accumulate oil. Microorganisms that accumulate more than 20% of oil on a cell dry weight basis can be called oleaginous microorganisms. Microbial oil, especially oil produced by yeasts, have a fatty acid composition similar to vegetable oil, mainly including C16 and C18 fatty acids, such as palmitic acid, stearic acid, and oleic acid. Microbial oil can replace expensive animal and vegetable oil as raw materials for production of biodiesel, and play an active role in promoting large-scale industrial production of biodiesel. In addition, the oleaginous microorganisms are short in fermentation period and not limited by seasonal climates, and utilize a wide range of carbon sources. Thus, they have good development prospects and will play an important role in the development of the biodiesel industry in future. However, the high cost of carbon sources in the culture of microorganisms and the low yield of microbial oil limit the development of microbial oil.

China is a big agricultural country, producing about 700 million tons of straw biomass every year. Together with forestry processing residues, China produces 2 billion tons of agricultural and forestry fiber biomass residues every year, but fails to effectively utilize this biomass. Biomass is rich in carbohydrates (cellulose and hemicellulose), which can be fully hydrolyzed to obtain glucose, so the requirements of the growth and metabolism of oleaginous yeasts for carbon sources can be satisfied. The use of these cellulosic sugar-containing hydrolysates to culture oleaginous yeasts may greatly reduce the production cost of microbial oil and provide the possibility to realize large-scale production of microbial oil.

In addition, the hydrolysates of agricultural and forestry biomass are rich in glucose, and also have monosaccharides such as xylose. However, there is glucose repression in most microbial metabolism processes. That is, when the medium contains glucose and xylose, the glucose will be utilized first, and the xylose will be utilized only when the glucose concentration is low. This mechanism will lead to technical problems such as long fermentation period, low utilization rate of cellulose resources, and high production cost in the utilization of hydrolysates. Therefore, it has become an important direction in the technical field of microbial oil to obtain high-yield oleaginous yeasts that can simultaneously utilize the mixed sugars of glucose and xylose.

SUMMARY

The disclosure provides a method for producing microbial oil by fermentation by culturing a high-yield oleaginous yeast in a cellulosic hydrolysate. According to the disclosure, a wild oleaginous yeast ZZ-46 is used as an original strain, cerulenin and TTC are used at a certain concentration as screening factors to perform primary screening of mutants, and the mutant strains of primary screening are subjected to high-throughput screening by Nile red fluorescence detection to finally obtain the high-yield oleaginous yeast with stable genetic traits. Besides, the cellulosic hydrolysate can be directly used to produce oil by fermentation, so that the oleaginous microorganism culture can utilize the raw materials from lignocellulose more efficiently, improves the technical economy of microbial oil production, and has wide application prospects.

The oleaginous yeast provided by the disclosure has been deposited in China Center for Type Culture Collection on May 21, 2020, with an accession number of CCTCC NO: M 2020139.

The disclosure provides a method of simultaneously utilizing xylose and glucose. The oleaginous yeast is added to a system containing xylose and glucose.

In an embodiment, the oleaginous yeast is fermented at 22-28° C. for 7-9 days.

In an embodiment, the oleaginous yeast is added to a fermentation system to produce oil by fermentation.

In an embodiment, a carbon source in the fermentation system comes from a hydrolyzed mixed sugar solution of a lignocellulose biomass raw material.

In an embodiment, a preparation method of the hydrolyzed mixed sugar solution includes:

(1) Alkali-catalyzed pretreatment of lignocellulose biomass raw material in organic solvent glycerin under atmospheric pressure: 90-150 g of dry lignocellulose biomass raw material is weighed and added to a 1000-5000 mL three-necked flask, followed by the addition of 900-1500 g of glycerin and 0.2% (w/w) of NaOH solid. The three-necked flask filled with a substrate is put into a constant temperature heating mantle, and meanwhile, the substrate is uniformly mixed by mechanical stirring and held at 200-250° C. for 8-12 min. After the completion of the reaction, 1000-1500 mL of tap water is poured into the flask to fully dissociate the substrate. Then, the mixture is filtered through a G1 sand core funnel. Next, the filter cake is washed with 1500-2000 mL of tap water twice and subjected to suction filtration. The finally obtained filter cake is the lignocellulose biomass substrate. The substrate is divided into two parts. One part is air-dried to a water content of 45-55% and stored at 2-4° C. The other part is oven-dried at 100-110° C. to the absolute weight.

(2) Enzymolysis of pretreated substrate: 10-20 g of the substrate with a water content of 45-55% is weighed and added to a 150-250 mL round-bottom flask. 0.5-1.0 mL of 2-5 $FPU \cdot g^{-1}$ cellulase on dry basis (the original enzyme solution is diluted with a citric acid buffer to 55-65 $FPU \cdot g^{-1}$) and additives, including 180-200 mg of PEG 4000, 350-400 mg of Triton X-100, 180-200 mg of tea saponin, 180-200 mg of bovine serum albumin and 20-25 mg of xylanase, are added, and the citric acid buffer (50 mM, pH 4.5-5.0) is added until the volume reaches 45-55 mL. At 10-12 h, 22-24 h and 34-36 h of the enzymolysis, 3.0-3.5 g, 2.5-3.0 g and 2.5-3.0 g of dry basis are respectively added. The enzymolysis is carried out at 45-55° C. for 68-78 h. After the completion of the enzymolysis, centrifuging is carried out at 8000-10000 $r \cdot min^{-1}$ for 4-6 min.

In an embodiment, the lignocellulose biomass includes agricultural straw and forestry processing residue waste raw materials.

In an embodiment, the oleaginous yeast with an $OD_{600}$ of 6-8 is added to the fermentation system at an addition amount of 5%-10% (v/v).

In an embodiment, a total sugar content in the fermentation system is 70-90 g/L. A nitrogen source is soybean peptone, $NH_4Cl$ or a yeast extract. Carbon/nitrogen=(273-373):1.

In an embodiment, a liquid volume of the fermentation solution in the fermentation system is 12%-20% (v/v).

In an embodiment, feeding is carried out in the fermentation process. The feeding is to add a mixture of glucose and xylose with a final concentration of 10-20 g/L, and a ratio of the glucose to the xylose in the mixture is (1-2):1.

In an embodiment, the oleaginous yeast is fermented at 22-28° C. and pH 6-8 for 7-9 days.

The disclosure provides a method for increasing oil yield. The oleaginous yeast is added to a fermentation system to produce oil by fermentation.

In an embodiment, the fermentation system contains a carbon source, and the carbon source is xylose and glucose.

In an embodiment, the fermentation system contains a carbon source, and the carbon source comes from a hydrolyzed mixed sugar solution of a lignocellulose biomass raw material.

In an embodiment, the oleaginous yeast seed solution with an $OD_{600}$ of 6-8 is added to the fermentation system at an addition amount of 5%-10% (v/v).

In an embodiment, a total sugar content in the fermentation system is 70-90 g/L. A nitrogen source is soybean peptone, $NH_4Cl$ or a yeast extract. Carbon/nitrogen=(273-373):1.

In an embodiment, a liquid volume of the fermentation solution in the fermentation system is 12%-20% (v/v), and the fermentation is carried out at 22-28° C. and pH 6-8 for 7-10 days.

In an embodiment, feeding is carried out in the fermentation process. The feeding is to add a mixture of glucose and xylose with a final concentration of 10-20 g/L, and a ratio of the glucose to the xylose in the mixture is (1-2):1.

In an embodiment, the fermentation system contains a carbon source, and the carbon source is xylose and glucose. The carbon source comes from a hydrolyzed mixed sugar solution of a lignocellulose biomass raw material. The oleaginous yeast seed solution with an $OD_{600}$ of 6-8 is added to the fermentation system at an addition amount of 5%-10% (v/v). A total sugar content in the fermentation system is 70-90 g/L. A nitrogen source is soybean peptone, $NH_4Cl$ or a yeast extract. Carbon/nitrogen=(273-373):1. A liquid volume of the fermentation solution in the fermentation system is 12%-20% (v/v), and the fermentation is carried out at 22-28° C. and pH 6-8 for 7-10 days. Feeding is carried out in the fermentation process. The feeding is to add a mixture of glucose and xylose with a final concentration of 10-20 g/L, and a ratio of the glucose to the xylose in the mixture is (1-2):1.

The disclosure further provides application of the oleaginous yeast, or the method of simultaneously utilizing xylose and glucose, or the method for increasing oil yield in producing oil in the fields of food, medicine, agriculture and chemical industry.

The agricultural and forestry lignocellulose biomass waste is a renewable resource with high cellulose and hemicellulose content, and has the advantages of wide sources and low cost. However, the hydrolysate of the agricultural and forestry lignocellulose biomass waste contains mixed sugars of glucose and xylose, and there is usually glucose repression in the culture of microorganisms in mixed sugars, resulting in long fermentation period and low efficiency. The high-yield oleaginous yeast obtained in the disclosure can simultaneously utilize glucose and xylose to accumulate a large amount of oil, so the sugar utilization efficiency and production intensity are enhanced. After 8 days of fed-batch fermentation, the oil yield can reach 31.33 g/L, and the oil content can reach 60.83%. The waste resources can be reutilized, and the production cost is reduced, so the oleaginous yeast has wide application prospects.

Biological Material Deposit

The oleaginous yeast provided by the disclosure is classified and named as *Trichosporon dermatis* L7, and has been deposited in China Center for Type Culture Collection on May 21, 2020, with an accession number of CCTCC NO: M 2020139, at the deposit address of Wuhan University, Wuhan, China.

DETAILED DESCRIPTION

Figure 1:
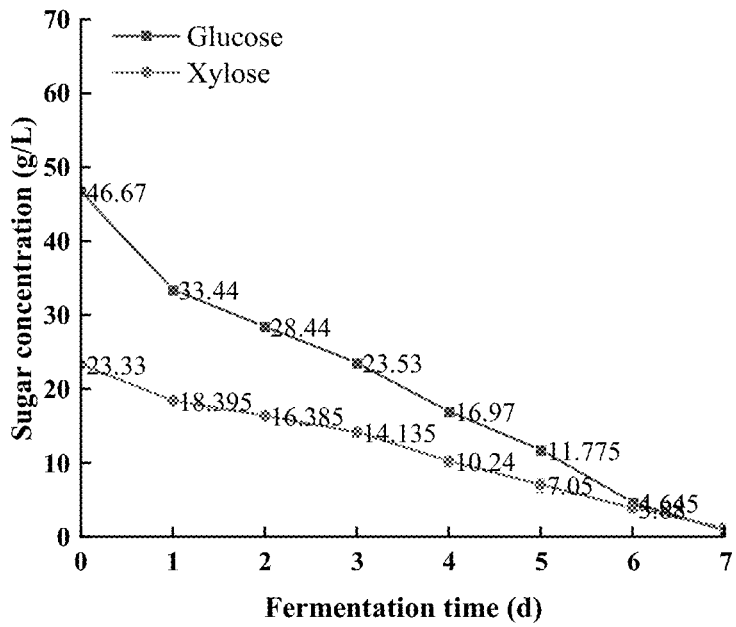
FIG. 1 shows synchronous sugar consumption curves of an original strain ZZ-46.
Figure 2:
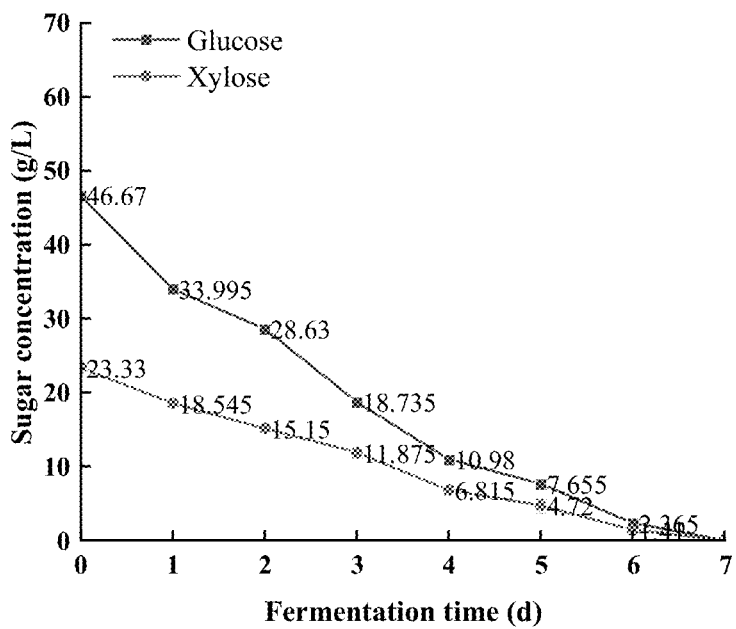
FIG. 2 shows synchronous sugar consumption curves of a strain L7.
Figure 3:
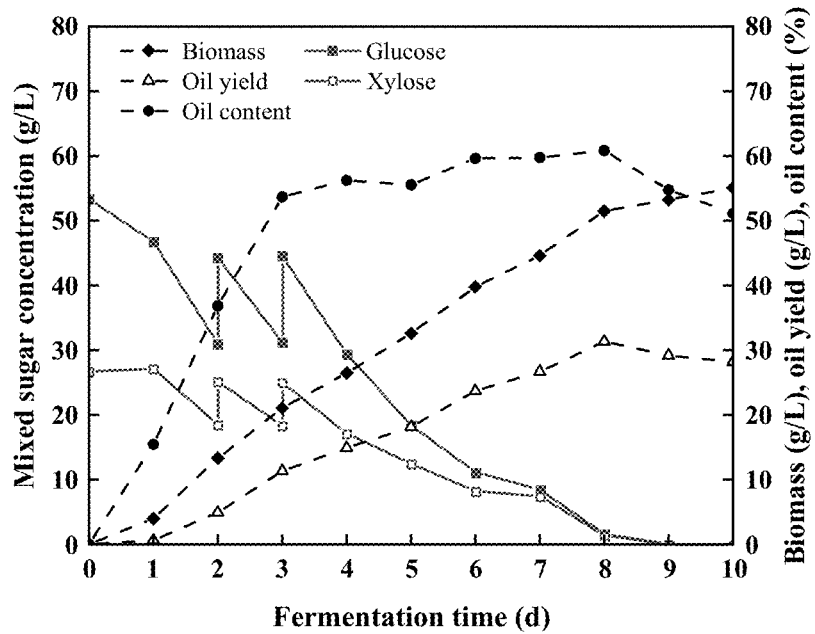
FIG. 3 shows results of fed-batch fermentation of the strain L7 in a 5 L fermentor. Fed carbon source glucose/xylose=2:1.
Figure 4:
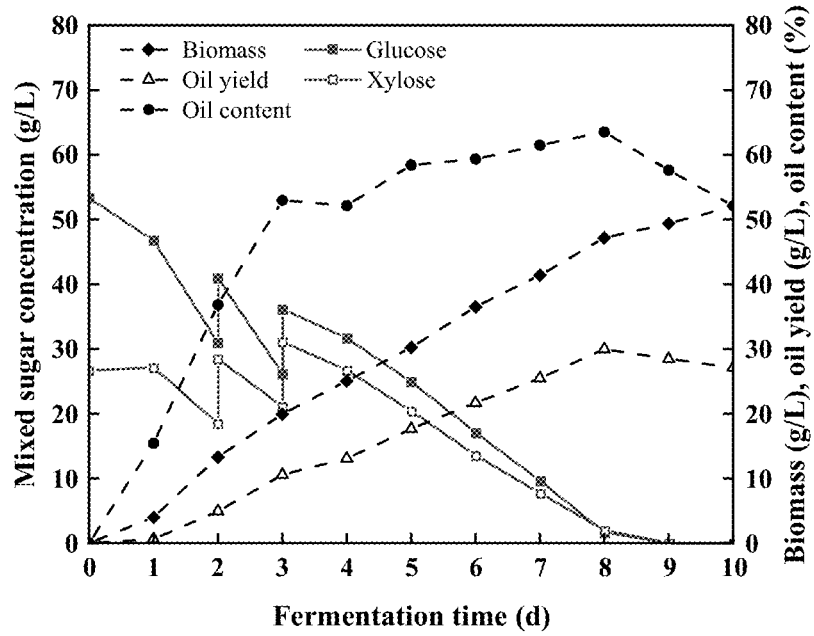
FIG. 4 shows results of fed-batch fermentation of the strain L7 in a 5 L fermentor. Fed carbon source glucose/xylose=1:1.

YPD solid medium: yeast extract 10 g/L, peptone 20 g/L, glucose 20 g/L and agar 15 g/L.

YPD seed medium: yeast extract 10 g/L, peptone 20 g/L and glucose 20 g/L.

Fermentation medium for secondary screening: carbon source: glucose 46.67 g/L and xylose 23.33 g/L; nitrogen source: yeast extract 0.75 g/L and $NH_4Cl$ 0.1 g/L; inorganic salt: $MgCl_2 \cdot 6H_2O$ 1 g/L and $Na_2SO_4$ 0.1 g/L; phosphate buffer: $KH_2PO_4$ 11.8 g/L and $K_2HPO_4 \cdot 3H_2O$ 3.7 g/L; and trace elements: $CaCl_2 \cdot 2H_2O$ 40 mg/L, $FeSO_4 \cdot 7H_2O$ 5.5 mg/L, citric acid monohydrate 5.2 mg/L, $ZnSO_4 \cdot 7H_2O$ 1 mg/L, $MnSO_4 \cdot H_2O$ 0.76 mg/L, and 18 mol $H_2SO_4$ 1.84× $10^{-3}$ mg/L, sterilized for later use.

The wild oleaginous yeast strain used in examples is *Trichosporon dermatis* ZZ-46, which has been deposited in China Center of Industrial Culture Collection in Nanyang City, with a strain number of NICC 30027.

Preparation of Bagasse Hydrolysate:

(1) Alkali-Catalyzed Pretreatment of Bagasse in Organic Solvent Glycerin Under Atmospheric Pressure 100 g of dry bagasse biomass is weighed and added to a 5000 mL three-necked flask, followed by the addition of 1000 g of glycerin and 0.2% (w/w) of NaOH solid. The three-necked flask filled with a substrate is put into a constant temperature heating mantle, and meanwhile, the substrate is uniformly mixed by mechanical stirring and held at 240° C. for 10 min. After the completion of the reaction, 1500 mL of tap water is poured into the flask to fully dissociate the substrate. Then, the mixture is filtered through a G1 sand core funnel. Next, the filter cake is washed with 2000 mL of tap water twice and subjected to suction filtration. The finally obtained filter cake is the bagasse substrate. The substrate is divided into two parts. One part is air-dried to a water content of 50% and stored at 4° C. The other part is oven-dried at 105° C. to the absolute weight.

(2) Enzymolysis of Pretreated Substrate 16 g of the substrate with a water content of 50% is weighed and added to a 250 mL round-bottom flask. 0.875 mL of 3 $FPU \cdot g^{-1}$ cellulase on dry basis (the original enzyme solution is diluted with a citric acid buffer to 60 FPU·g$^{-1}$) and additives, including 192 mg of PEG 4000, 356 mg of Triton X-100, 193 mg of tea saponin, 190 mg of bovine serum albumin and 21 mg of xylanase, are added, and the citric acid buffer (50 mM, pH 4.8) is added until the volume reaches 50 mL. At 12 h, 24 h and 36 h of the enzymolysis, 3.5 g, 3 g and 3 g of dry basis are respectively added. The enzymolysis is carried out by mechanical stirring at a speed of 150 r·min$^{-1}$ at a temperature of 50° C. for 72 h. After the completion of the enzymolysis, centrifuging is carried out at 10000 r·min$^{-1}$ for 5 min. The supernatant is taken, and the concentration of the glucose and xylose is determined.

(3) Dilution of Bagasse Hydrolysate

The contents of mixed sugars (208 g/L) in the bagasse hydrolysate obtained according to the above method are: glucose 140 g/L and xylose 68 g/L. According to the fermentation needs, the hydrolysate is diluted 3 folds with deionized water to 70 g/L or diluted 2.6 folds to 80 g/L, and pH is adjusted to 6 with NaOH.

Example 1: Mutation and Screening of Strains (1) Preparation of cell suspension: After the deposited wild oleaginous yeast strain was activated, single colonies were picked up and cultured in the YPD seed medium at 25° C. at 140 rpm for 36 h. 1 mL of cell suspension was taken and centrifuged at 8000 rpm for 5 min. The cells were collected, washed with sterile normal saline three times, and uniformly mixed in a vortexer such that the cells were dispersed. The cell suspension with a cell suspension concentration of $OD_{600}=1$ was adjusted for later use.

(2) ARTP mutagenesis: On a superclean bench, 10 ul of wild oleaginous yeast ZZ-46 cell suspension in step (1) was spread on a sterile metal slide. The metal slide was placed in a groove on an operating chamber stage of an ARTP mutagenesis instrument. Nitrogen was used as the working gas, the set power was 100 W, the treatment distance was 2 mm, the gas flow rate was 10 L/min, and the treatment time was 140 s.

(3) Plate pre-screening: The treated cell suspension was diluted at a dilution of $10^{-2}$, then spread on a screening plate containing $1.67 \times 10^{-3}$% (w/v) TTC and $4.107 \times 10^{-6}$ mol/L cerulenin, and cultured in a constant temperature incubator at 25° C. in the dark for 2 days.

(4) High-throughput screening: Big and red single colonies on the screening plate were picked up, placed in 48-well plates (1 mL medium/well) and cultured in a shaker at 25° C. at 200 rpm for 2 days. 100 uL of the cell suspension was transferred to 96-well plates. The $OD_{600}$ nm absorbance was detected with a microplate reader to characterize the cell concentration. 5 uL of Nile red solution was added to each well plate, the mixture was uniformly mixed and stained in the dark for 5 min, and fluorescence intensity was used to characterize the oil yield. The emission wavelength of detection was 485 nm, and the absorption wavelength was 595 nm. The fluorescence intensity was: the measured fluorescence intensity of the sample minus the background fluorescence intensity of the sample without Nile red.

(5) DES mutagenesis: The high-yield mutant strain obtained by the ARTP mutagenesis was activated and subjected to seed solution culturing to obtain a cell suspension. 2 mL of the cell suspension with $OD_{600}=1$ was taken. 2 mL of phosphate buffer with pH 7.0 was added, and then 0.2 mL of 50% diethyl sulfate-ethanol solution was added. The mixture was shaken at 25° C. for 70 min. After the completion of the treatment, 1 mL of 25% sodium thiosulfate was added to the reaction mixture to terminate the reaction.

(6) Screening after DES mutagenesis: The cell suspension after the DES treatment was subjected to plate pre-screening and high-throughput screening according to steps (3) and (4).

(7) Shake flask secondary screening: Single colonies were picked up from the high-yield strain obtained by primary screening, inoculated into the YPD seed medium, and cultured at 25° C. at 140 rpm for 36 h. The strain was inoculated into a 50 mL basic fermentation medium according to an inoculum size of 10% (v/v), and fermented at 25° C. at 140 rpm for 7 days. The fermentation solution was centrifuged, and the cells were collected. The biomass of the cells, the oil yield of the fermentation solution, and the oil content of the cells were determined. The results are shown in Table 1.

According to the relevant indexes determined, the strain L7 with better comprehensive effects was screened out and sent to China Center for Type Culture Collection to be deposited.

TABLE 1

Production performance of strains in secondary screening

| Strain | Biomass, g/L | Oil yield, g/L | Oil content, % |
|---|---|---|---|
| ZZ-46 | 20.12 | 8.59 | 42.67 |
| B6 | 21.75 | 10.31 | 47.40 |
| G1 | 19.22 | 8.67 | 45.08 |
| C4 | 18.54 | 8.74 | 47.12 |
| H4 | 18.84 | 9.06 | 48.08 |
| A4 | 19.05 | 8.92 | 46.79 |
| H6 | 20.76 | 9.07 | 43.67 |
| L7 | 22.66 | 11.44 | 50.49 |
| N7 | 22.24 | 11.02 | 49.57 |

The strain L7 was passaged (the culture method was the same as that in the shake flask secondary screening above). The biomass, oil yield and oil content of the first generation to the seventh generation were detected. As can be seen from Table 2, the biomass, oil yield and oil content of the mutant strain are all stable. The results show that the strain has good genetic stability.

TABLE 2

Passaging stability of strain L7

| Passage number | Biomass, g/L | Oil yield, g/L | Oil content, % |
|---|---|---|---|
| 1 | 22.61 | 11.42 | 50.51 |
| 2 | 22.70 | 11.53 | 50.77 |
| 3 | 22.94 | 11.60 | 50.57 |
| 4 | 22.54 | 11.38 | 50.48 |
| 5 | 21.85 | 11.23 | 51.38 |
| 6 | 22.73 | 11.53 | 50.71 |
| 7 | 22.99 | 11.54 | 50.17 |

Example 2: Fermentation Using Bagasse Hydrolysate

Composition of bagasse hydrolysate fermentation medium: The bagasse hydrolysate was diluted to a total sugar content of 70 g/L, pH was adjusted to 6, and no nitrogen source, inorganic salt or other substances were added.

Fermentation in bagasse hydrolysate: Single colonies of the strain L7 were inoculated into the YPD seed medium, cultured at 25° C. at 140 rpm for 36 h until $OD_{600}$ was 7.6, inoculated into the 50/250 mL (that is, a 250 mL conical flask was filled with 50 mL of fermentation medium)

bagasse hydrolysate medium according to an inoculum size of 10% (v/v), and fermented at 140 rpm at 25° C. for 7 days.

Oil production by strain fermentation: The strain L7 was fermented in the bagasse hydrolysate fermentation medium. The biomass, oil yield and oil content of the strain L7 were respectively 18.87 g/L, 9.26 g/L and 49.07%. The biomass, oil yield and oil content of the original strain ZZ-46 were respectively 15.21 g/L, 6.76 g/L and 44.46%. The biomass and oil yield were respectively increased by 24.06% and 36.98% as compared with the original strain.

Example 3: Fermentation Medium Using Bagasse Hydrolysate as Carbon Source

Composition of fermentation medium using bagasse hydrolysate as carbon source: The bagasse hydrolysate was diluted to a total sugar content of 70 g/L, pH was adjusted to 6, and the following components were added: nitrogen source: yeast extract 0.75 g/L and $NH_4Cl$ 0.1 g/L; inorganic salt: $MgCl_2 \cdot 6H_2O$ 1 g/L and $Na_2SO_4$ 0.1 g/L; phosphate buffer: $KH_2PO_4$ 11.8 g/L and $K_2HPO_4 \cdot 3H_2O$ 3.7 g/L; trace elements: $CaCl_2 \cdot 2H_2O$ 40 mg/L, $FeSO_4 \cdot 7H_2O$ 5.5 mg/L, citric acid monohydrate 5.2 mg/L, $ZnSO_4 \cdot 7H_2O$ 1 mg/L, $MnSO_4 \cdot H_2O$ 0.76 mg/L, and 18 mol $H_2SO_4$ $1.84 \times 10^{-3}$ mg/L.

Oil production by strain fermentation: Single colonies of the strain L7 were inoculated into the YPD seed medium, cultured at 25° C. at 140 rpm for 36 h until $OD_{600}$ was 7.6, inoculated into the 50/250 mL bagasse hydrolysate medium according to an inoculum size of 10% (v/v), and fermented at 140 rpm at 25° C. for 7 days.

After the strain L7 was fermented in the fermentation medium using the bagasse hydrolysate as the carbon source, the biomass, oil yield and oil content respectively reached 22.12 g/L, 11.18 g/L and 50.54%.

Example 4: Oil Production by Strain L7 Fermentation Under Shake Flask Optimized Conditions Composition of fermentation medium: The bagasse hydrolysate was diluted to a total sugar content of 80 g/L, soybean peptone was added as a nitrogen source, C/N=273:1 was kept, and the following components were further added: inorganic salt: $MgCl_2 \cdot 6H_2O$ 1 g/L and $Na_2SO_4$ 0.1 g/L; phosphate buffer: $KH_2PO_4$ 11.8 g/L and $K_2HPO_4 \cdot 3H_2O$ 3.7 g/L; trace elements: $CaCl_2 \cdot 2H_2O$ 40 mg/L, $FeSO_4 \cdot 7H_2O$ 5.5 mg/L, citric acid monohydrate 5.2 mg/L, $ZnSO_4 \cdot 7H_2O$ 1 mg/L, $MnSO_4 \cdot H_2O$ 0.76 mg/L, and 18 mol $H_2SO_4$ $1.84 \times 10^{-3}$ mg/L.

Oil production by strain fermentation: Single colonies of the strain L7 were inoculated into the YPD seed medium, cultured at 22° C. at 140 rpm for 36 h until $OD_{600}$ was 7.6, inoculated into the 40/250 mL bagasse hydrolysate medium according to an inoculum size of 10% (v/v), adjusted to pH 6 and fermented at 140 rpm at 22° C. for 8 days.

The biomass, oil yield and oil content reached 26.73 g/L, 14.00 g/L and 52.37%.

Example 5: Fed-Batch Fermentation Under Shake Flask Conditions

For specific implementation conditions, reference is made to Example 4. On such basis, four feeding manners were designed: the initial feeding point was the second day of the fermentation, the number of feeds was respectively 2, 3, 4 and 5, the feeding was carried out every other day, and the amount of each feed was 15 g/L (the fed nutrients were mixed sugars of glucose/xylose=2:1).

The specific manner was: Single colonies of the strain L7 were inoculated into the YPD seed medium, cultured at 25 at 140 rpm for 36 h until $OD_{600}$ was 7.6, inoculated into the 40/250 mL bagasse hydrolysate medium according to an inoculum size of 10% (v/v), and fermented at 140 rpm at 22° C. for 9 days.

2 feeds: respectively on Day 2 and Day 3;
3 feeds: respectively on Day 2, Day 3 and Day 4;
4 feeds: respectively on Day 2, Day 3, Day 4 and Day 5; and
5 feeds: respectively on Day 2, Day 3, Day 4, Day 5 and Day 6.

For each feed, mixed sugars (glucose/xylose=2:1) with a final concentration of 15 g/L were added.

The fermentation results are shown in Table 3. The results show that the two feeds obtain the maximum oil yield and oil content, respectively 20.21 g/L and 57.93%. At this time, the biomass is 34.89 g/L. The oil yield, the oil content and the biomass are respectively increased by 44%, 11% and 31% as compared with the batch shake flask culture.

TABLE 3

Oil production performance of strain L7 under different numbers of feeds

| Number of feeds | Biomass, g/L | Oil yield, g/L | Oil content, % |
|---|---|---|---|
| 2 | 34.89 | 20.21 | 57.93 |
| 3 | 35.92 | 19.66 | 54.71 |
| 4 | 36.89 | 19.21 | 52.07 |
| 5 | 32.77 | 18.21 | 55.58 |

Example 6: Oil Production by L7 Strain Fermentation in 5 L Fermentor (1) Batch Fermentation in Fermentor For the specific composition of the fermentation medium and the specific implementation, reference is made to Example 4.

Oil production by strain fermentation: Single colonies of the strain L7 were inoculated into the YPD seed medium, cultured at 25° C. at 140 rpm for 36 h until $OD_{600}$ was 7.6, inoculated into the 2 L bagasse hydrolysate medium according to an inoculum size of 10% (v/v), adjusted to pH 6 and fermented at 22° C. for 5 days. In the fermentation process, 2 M NaOH was used to adjust pH and keep the pH stable at 6, the rotational speed was related to DO, and the DO was kept at 30% or above. An organic silicone defoamer was added to control foam generated in the fermentation process.

The fermentation results show that the biomass, oil yield and oil content are respectively 33.33 g/L, 18.11 g/L and 54.34%.

(2) Fed-Batch Culture in Fermentor

The feed solution of glucose/xylose=2:1 or glucose/xylose=1:1 was fed for fermentation.

Oil production by strain fermentation: Single colonies of the strain L7 was inoculated into the YPD seed medium, cultured at 25° C. at 140 rpm for 36 h until $OD_{600}$ was 7.6, inoculated into the 2 L bagasse hydrolysate medium according to an inoculum size of 10% (v/v), adjusted to pH 6 and fermented at 22° C. In the fermentation process, 2 M NaOH was used to adjust pH and keep the pH stable at 6, the rotational speed was related to DO, and the DO was kept at 30% or above. An organic silicone defoamer was added to control foam generated in the fermentation process.

The feeding was carried out on Day 2 and Day 3. The fed nutrients were mixed sugars (glucose/xylose=2:1, or glucose/xylose=1:1) with a final concentration of 20 g/L.

On Day 8 of the fermentation, the oil content reached the maximum. When glucose/xylose=2:1, the oil yield could reach 31.33 g/L.

TABLE 4

Oil production performance of strain L7 under different ratios of fed nutrients

| Fed mixed sugars | Biomass, g/L | Oil yield, g/L | Oil content, % |
|---|---|---|---|
| Glucose/xylose = 2:1 | 51.50 | 31.33 | 60.83% |
| Glucose/xylose = 1:1 | 47.17 | 29.97 | 63.53% |

Comparative Example 1

For the specific implementation, reference is made to Example 4. The difference was that the total sugar content 80 g/L was replaced with 50 g/L, 60 g/L, 70 g/L, 90 g/L and 100 g/L. The biomass, oil yield and oil content obtained after fermentation are shown in Table 5.

TABLE 5

Oil production performance of strain L7 under different total sugar contents

| Total sugar content, g/L | Biomass, g/L | Oil yield, g/L | Oil content, % |
|---|---|---|---|
| 50 | 19.19 | 5.65 | 29.44 |
| 60 | 22.78 | 6.58 | 28.88 |
| 70 | 23.53 | 6.97 | 29.62 |
| 80 | 24.11 | 8.10 | 33.59 |
| 90 | 25.00 | 7.46 | 29.84 |
| 100 | 22.23 | 6.44 | 28.97 |

Comparative Example 2

For the specific implementation, reference is made to Example 4. The difference was that the nitrogen source soybean peptone was replaced with $NH_4Cl$, $(NH_4)_2SO_4$, yeast extract, fish meal peptone and $NH_4Cl$ yeast extract. The biomass, oil yield and oil content obtained after fermentation are shown in Table 6.

TABLE 6

Oil production performance of strain L7 under different nitrogen source conditions

| Nitrogen source | Biomass, g/L | Oil yield, g/L | Oil content, % |
|---|---|---|---|
| $NH_4Cl$ | 18.80 | 6.26 | 33.29 |
| $(NH_4)_2SO_4$ | 17.87 | 5.65 | 31.61 |
| Yeast extract | 18.40 | 5.91 | 32.11 |
| Fish meal peptone | 18.19 | 5.70 | 31.33 |
| Soybean peptone | 19.93 | 7.65 | 38.38 |
| $NH_4Cl$ yeast extract | 17.77 | 5.42 | 30.51 |

Comparative Example 3

For the specific implementation, reference is made to Example 4. The difference was that C/N=273:1 was replaced with 123:1, 223:1, 323:1, 373:1, 423:1 and 523:1. The biomass, oil yield and oil content obtained after fermentation are shown in Table 7.

TABLE 7

Oil production performance of strain L7 under different C/N conditions

| C/N | Biomass, g/L | Oil yield, g/L | Oil content, % |
|---|---|---|---|
| 123:1 | 16.55 | 2.23 | 13.47 |
| 223:1 | 17.88 | 4.76 | 26.62 |
| 273:1 | 20.24 | 7.04 | 34.78 |
| 323:1 | 19.22 | 6.53 | 33.98 |
| 373:1 | 18.87 | 6.26 | 33.17 |
| 423:1 | 17.53 | 5.63 | 32.11 |
| 523:1 | 17.89 | 5.76 | 32.20 |

Comparative Example 4

For the specific implementation, reference is made to Example 4. The difference was that the inoculum size 10% (v/v) was replaced with 5% (v/v), 7.5% (v/v), 12.5% (v/v) and 15% (v/v). The biomass, oil yield and oil content obtained after fermentation are shown in Table 8.

TABLE 8

Oil production performance of strain L7 under different inoculum sizes

| Inoculum size, % | Biomass, g/L | Oil yield, g/L | Oil content, % |
|---|---|---|---|
| 5 | 20.68 | 10.01 | 48.41 |
| 7.5 | 21.67 | 10.86 | 50.10 |
| 10 | 23.28 | 9.98 | 42.86 |
| 12.5 | 19.30 | 6.94 | 35.98 |
| 15 | 18.22 | 6.02 | 33.02 |

Comparative Example 5

For the specific implementation, reference is made to Example 4. The difference was that the liquid volume 40/250 mL was replaced with 30/250 mL, 50/250 mL, 60/250 mL and 70/250 mL. The biomass, oil yield and oil content obtained after fermentation are shown in Table 9.

TABLE 9

Oil production performance of strain L7 under liquid volumes

| Liquid volume, mL | Biomass, g/L | Oil yield, g/L | Oil content, % |
|---|---|---|---|
| 30 | 26.05 | 11.62 | 44.62 |
| 40 | 24.05 | 10.75 | 44.71 |
| 50 | 23.67 | 10.99 | 46.44 |
| 60 | 18.74 | 8.03 | 42.86 |
| 70 | 15.98 | 6.16 | 38.54 |

Comparative Example 6

For the specific implementation, reference is made to Example 4. The difference was that the pH 6 was replaced with pH 4, pH 5, pH 7 and pH 8. The biomass, oil yield and oil content obtained after fermentation are shown in Table 10.

TABLE 10

Oil production performance of strain L7 under different pH

| pH | Biomass, g/L | Oil yield, g/L | Oil content, % |
|---|---|---|---|
| 4 | 11.32 | 3.91 | 34.54 |
| 5 | 13.30 | 5.15 | 38.70 |
| 6 | 21.89 | 9.44 | 43.14 |
| 7 | 21.67 | 8.77 | 40.47 |
| 8 | 18.34 | 6.97 | 38.01 |

Comparative Example 7

For the specific implementation, reference is made to Example 4. The difference was that the temperature 22° C. was replaced with 25° C., 28° C. and 31° C. The biomass, oil yield and oil content obtained after fermentation are shown in Table 11.

TABLE 11

Oil production performance of strain L7 under different fermentation temperatures

| Temperature, ° C. | Biomass, g/L | Oil yield, g/L | Oil content, % |
|---|---|---|---|
| 22 | 21.67 | 9.37 | 43.26 |
| 25 | 22.83 | 10.31 | 45.18 |
| 28 | 19.06 | 6.36 | 33.37 |
| 31 | 13.59 | 2.94 | 21.64 |

Comparative Example 8

For the specific implementation, reference is made to Example 4. The difference was that the fermentation time 8 days was replaced with 7 days and 9 days. The biomass, oil yield and oil content obtained after fermentation are shown in Table 12.

TABLE 12

Oil production performance of strain L7 under different fermentation time

| Fermentation time, d | Biomass, g/L | Oil yield, g/L | Oil content, % |
|---|---|---|---|
| 7 | 25.97 | 12.71 | 48.94 |
| 8 | 26.73 | 14.00 | 53.37 |
| 9 | 26.90 | 13.87 | 51.56 |

Although the disclosure has been disclosed as above in the preferred examples, it is not intended to limit the disclosure. Any person skilled in the art can make various changes and modifications without departing from the spirit and scope of the disclosure. Therefore, the protection scope of the disclosure should be as defined in the claims.

What is claimed is:

1. A method for producing oil by simultaneously utilizing xylose and glucose, which comprises:
    providing a fermentation system comprising bagasse hydrolysate, wherein the bagasse hydrolysate comprises xylose and glucose from a hydrolyzed mixed sugar solution of a lignocellulose biomass raw material;
    adding an oleaginous yeast or a culture thereof to the system; and
    incubating the fermentation system under conditions suitable to cause fermentation, thereby producing the oil at a final concentration of at least 11.18 g/L;
    wherein the oleaginous yeast is classified and named as *Trichosporon dermatis* which has been deposited in China Center for Type Culture Collection on May 21, 2020, with an accession number of CCTCC NO: M 2020139.

2. The method according to claim 1, wherein fermentation of xylose and glucose by the oleaginous yeast is performed at 22° C. to 28° C. for 7 to 10 days.

3. The method according to claim 1, further comprising adding a seed solution of the oleaginous yeast with an $OD_{600}$ of 6 to 8 to the fermentation system at an amount of 5% to 10%.

4. The method according to claim 1, wherein:
    a total sugar content in the fermentation system is 70 g/L to 90 g/L;
    a nitrogen source is $NH_4Cl$; and
    the ratio of carbon to nitrogen is 273:1 to 373:1.

5. The method according to claim 1, wherein a liquid volume of a fermentation solution in the fermentation system is 12% to 20%, and wherein the fermentation is carried out at 22° C. to 28° C. and a pH of 6 to 8 for a period of 7 to 10 days.

6. The method according to claim 1, comprising carrying out feeding in the fermentation process; and the feeding is by adding a mixture of glucose and xylose with a final concentration of 10 g/L to 20 g/L, and a ratio of the glucose to the xylose in the mixture is 1:1 to 2:1.

7. The method according to claim 1, wherein:
    the fermentation system further comprises a carbon source, and wherein the carbon source is xylose and glucose;
    the carbon source is from a hydrolyzed mixed sugar solution of a lignocellulose biomass raw material;
    the oleaginous yeast seed solution with an $OD_{600}$ of 6 to 8 is added to the fermentation system at an amount of 5% to 10%;
    a total sugar content in the fermentation system is 70 g/L to 90 g/L;
    a nitrogen source is soybean peptone, $NH_4Cl$, or a yeast extract;
    the ratio of carbon to nitrogen is 273:1 to 373:1;
    a liquid volume of the fermentation solution in the fermentation system is 12% to 20%, and wherein the fermentation is performed at 22° C. to 28° C. and at a pH of 6 to 8 for a period of 7 to 10 days; and
    feeding is performed in the fermentation process, wherein the feeding comprises adding a mixture of glucose and xylose to a final concentration of 10 g/L to 20 g/L, and wherein the ratio of the glucose to the xylose in the mixture is 1:1 to 2:1.

* * * * *